United States Patent [19]
Kuo et al.

[11] Patent Number: 5,278,071
[45] Date of Patent: Jan. 11, 1994

[54] BENCH TEST METHOD FOR RATING THE CORROSION INHIBITING ABILITY OF AN OLEAGINOUS FLUID

[75] Inventors: Cheng-Chueh Kuo; David M. Marchand, both of Baton Rouge, La.

[73] Assignee: Ethyl Corporation, Richmond, Va.

[21] Appl. No.: 878,970

[22] Filed: May 6, 1992

[51] Int. Cl.$^5$ .................... G01N 17/00; G01N 33/26
[52] U.S. Cl. .......................... 436/6; 422/53; 73/53.06
[58] Field of Search ............... 436/2, 6; 422/20, 53; 73/53.01, 61.62, 104, 53.06

[56] References Cited

U.S. PATENT DOCUMENTS

| | | | |
|---|---|---|---|
| 3,019,090 | 1/1962 | Renshaw et al. | 436/6 |
| 3,110,567 | 11/1963 | Hughes | 436/6 |
| 4,229,284 | 10/1980 | White et al. | 422/12 X |
| 4,347,285 | 8/1982 | Batdorf | 428/332 |
| 4,846,986 | 7/1989 | Trivett | 252/49.5 |
| 5,012,116 | 4/1991 | Russell | 250/572 |

OTHER PUBLICATIONS

Perry, John H., *Chemical Engineers' Handbook*, pp. 23-48-23-49, 1963.
ASTM-*Multicylinder Test Sequences for Evaluating Automotive Engine Oils*, Part 1: Sequence 11D, STP 315H (1980).
ASTM D 665-83, "Standard Test Method for Rust-Preventing Characteristics of Inhibited Mineral Oil in the Presence of Water", pp. 244-250 (1983).
ASTM D 664-87, "Standard Test Method for Acid Number of Petroleum Products by Potentiometric Titration", pp. 237-243 w/2 p. Appendix (1987).

*Primary Examiner*—Lyle A. Alexander
*Assistant Examiner*—Robert Carpenter
*Attorney, Agent, or Firm*—David E. LaRose

[57] ABSTRACT

A bench-test method which correlates well with other more costly engine test methods, and which can be used to screen oleaginous formulation prior to performing expensive engine tests. The method comprises a) contacting ball bearing(s) having a smooth surface area with an oleaginous fluid to be screened; b) treating the oleaginous fluid during contacting with corrosive vapor for a period of time and at a temperature sufficient to form a metal oxide coating on the ball bearing(s) surface; and c) visually rating the metal oxide coating on the ball bearings.

16 Claims, 5 Drawing Sheets

1HR. 35MIN.

1C1 1:35 1040

5A2 1:35 1040

8C2 1:35 1040

2 HR. 0 MIN.

8.82 1C1 2:00 1040

7.87 5A2 2:00 1040

1HR. 35MIN.

1C1 1:35 52100

5A2 1:35 52100

8C2 1:35 52100

2 HR. 0 MIN.

1C1 2:00 52100

5A2 2:00 52100

BENCH TEST METHOD FOR RATING THE CORROSION INHIBITING ABILITY OF AN OLEAGINOUS FLUID

BACKGROUND

This invention relates to a bench test method for oleaginous fluids. More specifically, this invention provides a reliable bench test method for screening oleaginous fluid compositions and lubricant formulations for their ability to inhibit engine rust formation prior to more extensive engine testing.

Until now, the oil and automotive industry has relied on a number of standardized engine tests to determine the beneficial or detrimental effects of additives in various oleaginous fluid compositions, specifically for determination of the ability of oleaginous formulations to inhibit engine rust. Numerous engine tests are usually required to qualify a particular oleaginous formulation before it is accepted by the oil and/or automotive industry. Typically, the engine tests are quite expensive and time consuming. One particularly useful engine test is the Sequence IID engine test performed in accordance with ASTM STP 315H Part I. While the IID engine test has been relied on for a number of years, the engines utilized in the test are designed for use with leaded fuels. Such leaded fuel engine designs are obsolete and thus are no longer in production. Current engines are designed to run exclusively on unleaded fuels. Likewise, leaded fuel is becoming less readily available. There is a need therefore for a reliable, yet less costly means for determining how a particular oleaginous formulation will perform in an engine under actual operating conditions.

SUMMARY OF THE INVENTION

A reliable bench-test method has now been found which correlates well with other more costly engine test methods, and which can be used to screen oleaginous formulations prior to performing expensive engine tests. The method comprises a) contacting ball bearing(s) having smooth surface area with an oleaginous fluid to be screened; b) treating the oleaginous fluid during contacting with corrosive vapor for a period of time and at a temperature sufficient to form a metal oxide coating on the ball bearing(s) surface; and c) visually rating the metal oxide coating on the ball bearings.

This invention has not only reduced the need for performing expensive engine tests on all oleaginous formulations, but has provided a means to screen multiple formulations over a relatively short period of time. Other advantages will be evident from the ensuing description.

DETAILED DESCRIPTION OF THE INVENTION

Figure 1:
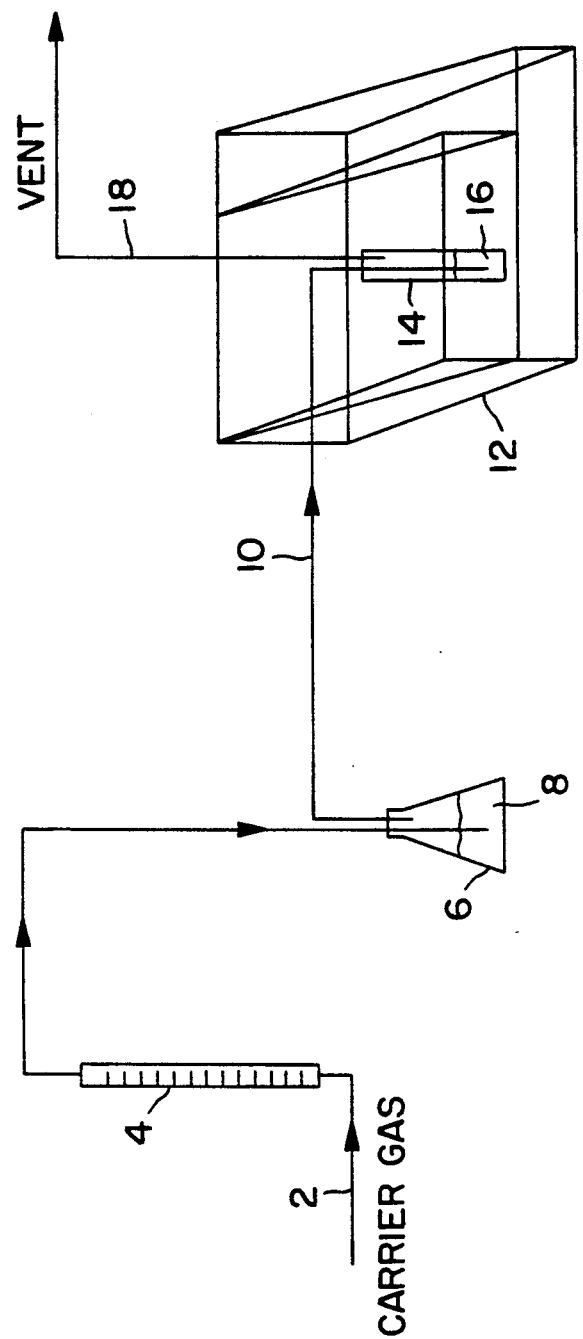
FIG. 1 is an illustration, not to scale, of apparatus for performing the bench test method described herein.

In a preferred embodiment, this invention provides a bench test method for determining the ability of one or more oleaginous fluid composition(s) to inhibit corrosion comprising a) providing (i) one or more ball bearings having smooth surface area, (ii) an oleaginous fluid composition, and (iii) corrosive vapor; b) immersing the ball bearing(s) in an amount of oleaginous fluid; c) contacting the fluid with the corrosive vapor at a first temperature and for a first period of time; d) maintaining the contacted fluid containing the bearing(s) for a second period of time and at a second temperature sufficient to induce oxidation of the bearing(s) surface; and e) comparing the bearing(s) with a set of reference bearing(s) thereby determining the ability of the oleaginous fluid composition to inhibit corrosion.

In another preferred embodiment, this invention relates to a bench-test apparatus for evaluating oleaginous fluid compositions comprising: a) an oleaginous fluid contact vessel; b) a means for generating corrosive vapor for contact with the oleaginous fluid in the contact vessel; and c) a means for maintaining the contact vessel containing the oleaginous fluid at one or more temperatures during and subsequent to contacting with corrosive vapor.

A key feature of the methods and apparatus of this invention is the discovery that metal samples in the form of ball bearings having a smooth surface area can be contacted with oleaginous formulations under an conditions which simulate engine operating conditions. Since the ball bearings have a surface which is smoother and more uniform than other metal samples such as pins used in the Modified ASTM D-664 Rust Test Method, the results obtained are more reproducible. The ball bearings used in this invention are carbon steel, chrome steel or both. The carbon steel and chrome steel ball bearings conform in general to AISI 1040 and AISI 52100 respectively, having a smooth surface area and have the following average composition.

| Element | Carbon Steel Wt.% | Chrome Steel Wt.% |
| --- | --- | --- |
| Carbon | 0.401 | 1.035 |
| Sulfur | 0.024 | 0.010 |
| Manganese | 0.530 | 0.280 |
| Phosphorus | 0.011 | 0.017 |
| Silicon | 0.077 | 0.230 |
| Copper | 0.078 | 0.139 |
| Nickel | 0.038 | 0.106 |
| Chromium | 0.049 | 1.400 |
| Vanadium | <0.010 | <0.010 |
| Molybdenum | 0.013 | 0.031 |
| Aluminum | 0.046 | 0.025 |
| Iron | balance | balance |

By smooth surface area it is meant that the ball bearings have an arithmetical average surface roughness of less than about 5 microns, preferably less than about 4 microns, and most preferably, about 2 microns or less. While it is preferred to use ball bearings having the above average composition and smooth surfacer area, other ball bearings may be used with this invention provided the surface of the bearings is uniform and has a surface roughness of less than about 3 microns.

Typically, one or more ball bearings are submerged in the oleaginous fluid to be tested. It is preferred that more than one ball bearing be used, more preferably more than two ball bearings, and most preferably about 5 ball bearings. Using more than one ball bearing assures that the observed results are not simply due to a poor quality ball bearing sample and/or that the oleaginous fluid was not homogeneously treated with the corrosive vapor during the test procedure.

The oleaginous fluid used in performing the test is a partially or fully formulated crankcase oil containing additive(s) selected from detergent/dispersant, antioxidant, antiwear agent, friction modifier, anti-foam agent, rust inhibitor, surfactant, viscosity index improver, pour point depressant, and the like, or any combination of two or more of the foregoing. Preferably the oleaginous fluid is a fully formulated oleaginous fluid. Suitable detergents/dispersants include any of the one or more hydrocarbyl substituted succinimide based detergent/dispersants, as well as olefin substituted polyamine detergent/dispersants. Corrosion inhibitors include dimer and trimer acids, such as are produced from tall oil fatty acids, oleic acid, linoleic acid, or the like. Products of this type are currently available from various commercial sources, such as for example, the dimer and trimer acids sold under the HYSTRENE trademark by the Humko Chemical Division of Witco Chemical Corporation and under the EMPOL trademark by Emery Chemicals. Another useful type of corrosion inhibitor for use in the practice of this invention are the alkenyl succinic acid and alkenyl succinic anhydride corrosion inhibitors such as, for example, tetrapropenylsuccinic acid, tetrapropenylsuccinic anhydride, tetradecenylsuccinic acid, tetradecenyl-succinic anhydride, hexadecenylsuccinic acid, hexadecenylsuccinic anhydride, and the like. Also useful are the half esters of alkenyl succinic acids having 8 to 24 carbon atoms in the alkenyl group with alcohols such as the polyglycols. Preferred materials are the succinic acids or derivatives thereof represented by the formula:

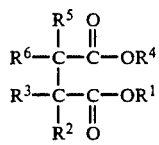

wherein each of $R^2$, $R^3$, $R^5$ and $R^6$ is, independently, a hydrogen atom or a hydrocarbyl group containing 1 to 30 carbon atoms, and wherein each of $R^1$ and $R^4$ is, independently, a hydrogen atom, a hydrocarbyl group containing 1 to 30 carbon atoms, or an acyl group containing from 1 to 30 carbon atoms.

The groups $R^1$, $R^2$, $R^3$, $R^4$, $R^5$, and $R^6$ when in the form of hydrocarbyl groups, can be, for example, alkyl, cycloalkyl or aromatic containing groups. Preferably $R^1$, $R^2$, $R^3$, $R^4$ and $R^5$ are hydrogen or the same or different straight-chain or branched-chain hydrocarbon radicals containing 1-20 carbon atoms. Most preferably, $R^1$, $R^2$, $R^3$, $R^4$, and $R^5$ are hydrogen atoms. $R^6$ when in the form of a hydrocarbyl group is preferably a straight-chain or branched-chain saturated hydrocarbon radical.

Most preferred is an alkenyl succinic acid of the above formula wherein $R^1$, $R^2$, $R^3$, $R^4$ and $R^5$ are hydrogen and $R^6$ is a tetrapropenyl group.

Other ingredients in the oleaginous formulations may include anti-wear agents, extreme pressure agents, antioxidants, metal deactivators and the like.

To perform the bench test as disclosed herein an oleaginous fluid is placed in a contact vessel and one or more ball bearings are placed in the oleaginous fluid. The oleaginous fluid is then treated for a period of time with corrosive vapor. The corrosive vapor may be comprised of one or more acid vapors formed by passing a carrier gas through a vessel containing an aqueous protonoic acid mixture. Such aqueous acid mixtures may be selected from HCl solutions, HBr solutions, HF solutions, $HNO_3$ solutions, $H_2SO_4$ solutions, phosphoric acid, phosphorous acid, and the like; or aqueous organic acid mixtures containing formic, acetic, malonic, maleic, and the like. Particularly preferred are aqueous $HNO_3$ solutions and most preferably aqueous $HNO_3$ solutions containing about 70 to about 75 weight percent nitric acid.

Carrier gases used for generating the corrosive vapor include air, oxygen, nitrogen, argon, helium, and the like. Most preferably, air is used to generate the corrosive vapor from the acid mixture. In a particularly preferred embodiment, the corrosive vapor is comprised of at least about 0.01 volume percent nitric acid vapor, more preferably at least about 0.2 volume percent nitric acid vapor, and most preferably at least about 0.5 volume percent nitric acid vapor. Water vapor comprises about 0.5 volume percent of the corrosive vapor thus generated when using an aqueous acid solution and a carrier gas at about room temperature.

Once formed the corrosive vapor is contacted with the oleaginous fluid in the contact vessel at a first temperature and for a first period of time. The first contact time and temperature should be sufficient to dissolve a substantial amount of corrosive vapor in the oleaginous fluid which amount is sufficient to induce oxidation of the ball bearing(s) surface. Thus the first contact time is desirably longer than 30 minutes, more preferably longer than 1 hour and most preferably from about 1 to about 4 hours. During the contacting it is highly desirable to agitate the oleaginous fluid containing the ball bearings in order to maintain an essentially homogenous mixture of fluid and dissolved corrosive vapor in contact with the ball bearings. The first temperature during the first contact time is generally in the range of from about 20° C. to about 60° C.

Subsequent to contacting the oleaginous fluid with the corrosive vapor, the fluid containing the ball bearings is maintained for a second period of time and at a second temperature sufficient to induce oxidation of the bearing(s) surface. The temperature is suitably above room temperature, preferably above about 35° C. and most preferably about 45° to about 55° C. Higher temperatures may be used, however they are not required.

The second period of time for maintaining the bearings in contact with the treated oleaginous solution is not critical to the invention. However, it is highly preferred to maintain contact at the second temperature for more than 5 hours, preferably more than 10 hours, and most preferably from about 14 to about 18 hours. Longer times for maintaining contact may be used but are not necessary to the methods of this invention.

During the maintaining of the bearings in the oleaginous fluid for the second period of time, it is desirable to agitate the oleaginous fluid contact vessel containing the fluid and the bearings. Agitation assures essentially homogenous contact of the bearings surfaces with the treated oleaginous fluid.

Subsequent to the second period of time, the bearings are removed from the oleaginous fluid being tested and observed for surface corrosion. Generally, the bearings are cleaned prior to observing the amount of corrosion.

Any suitable solvent may be used for cleaning the ball bearings such as hexane, heptane, xylene, toluene, and the like. A visual comparison of the ball bearings with pictures of bearings contacted with standard reference oils which have been likewise treated with corrosive vapor, indicates the ability of the oil being tested to inhibit corrosion.

In order to further illustrate the invention, reference is made to FIG. 1. FIG. 1 is an illustration, in schematic form, of a bench test apparatus for performing the bench test procedure described herein. A carrier gas such as dry air is fed via conduit 2 through flowmeter 4 to a means for generating corrosive vapor comprised of a vessel 6 and an aqueous acid solution 8. It is preferred that the carrier gas be fed to vessel 6 below the level of aqueous acid solution 8 in the vessel. The corrosive vapor thus generated is then fed via conduit 10 to one or more contact vessel(s) 14 containing the oleaginous fluid 16 to be tested. Again it is preferred that the corrosive vapor be fed to the contact vessel(s) 14 below the surface of fluid 16 in the vessel(s). The contact vessel(s) is vented via conduit 18 to the atmosphere or to a solution for neutralization of the vent gases (not shown). During the contacting, the contact vessel(s) 14 is maintained at constant temperature by temperature control means 12. It is highly preferred that contact vessel(s) 14 be agitated during the contacting and holding periods. Agitation of the contact vessel(s) may be performed by use of a vibrating temperature control means, described herein, or other means known in the art.

The following example illustrates this invention.

Example 1

Bench Test Method

Carbon steel balls (25 balls, 5.55 mm in diameter, AISI 1040) and Chrome steel balls (25 balls, 5.55 mm in diameter, AISI 52100) having a surface roughness of 2 microns are cleaned with heptane in an ultrasonic cleaning bath for 1 minute. Typically, the balls are cleaned with heptane several times before drying. The balls are then dried with nitrogen and weighed to obtain an initial weight. Ten contact tubes (30 mL capacity) having a two hole stopper are filled with 10 mL of oil to be tested and five of the carbon steel or chrome steel balls. Three 500 mL Erlenmeyer flasks are each filled with 250 mL of 71 weight percent nitric acid. A two hole stopper is placed in the mouth of each of the 500 mL flasks. Compressed air at 35 psia (241 KPa) is bubbled via a flowmeter at the rate of 118 cubic centimeters per minute into nitric acid in each of the 500 mL flasks in succession. A conduit containing nitric acid vapors leading from the third flask is directed into the oil to be tested so that the acid vapors bubble through the oil for 1.5 to 2 hours. Subsequent to bubbling the nitric acid vapors into the oil, the 10 mL tubes containing the oil and balls are maintained at about 50° C. in a controlled temperature shaker (commercially available from Lab-Line, Environ-Shaker Model 3528) for 16 hours. Subsequent to the 16 hour hold period, the balls are removed from the oil, cleaned with heptane, dried with nitrogen and weighed and visually inspected for corrosion. The corrosion observed is compared to corrosion obtained by the above procedure with a series of standard reference oils. According to the ASTM IID Sequence engine test procedure, balls having a rust rating of 0 are completely rusted, while balls having a rust rating of 10 are essentially free of rust.

Figure 2:
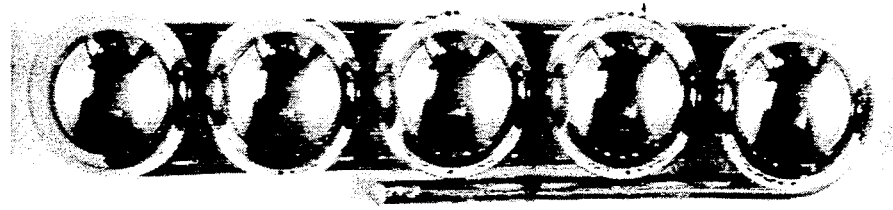
FIGS. 2 through 6 are photographs of carbon steel balls which have been immersed in various reference oils and treated with corrosive vapor for a period of time.
Figure 3:
Figure 4:

In FIGS. 2, 3, and 4, carbon steel balls were treated in accordance with the above procedure by bubbling nitric acid vapor into oils containing the balls for 1 hour and 35 minutes. FIG. 2 is a photograph of carbon steel balls which have been treated in accordance with the above procedure in a 1C1 reference oil having a ASTM IID Sequence engine test average rust rating of 8.82. FIG. 3 is a photograph of carbon steel balls treated in a 5A2 reference oil having an average IID rust rating of 7.87. And FIG. 4 is a photograph of carbon steel balls treated in an 8C2 reference oil having an average IID rust rating of 5.42.

Figure 5:
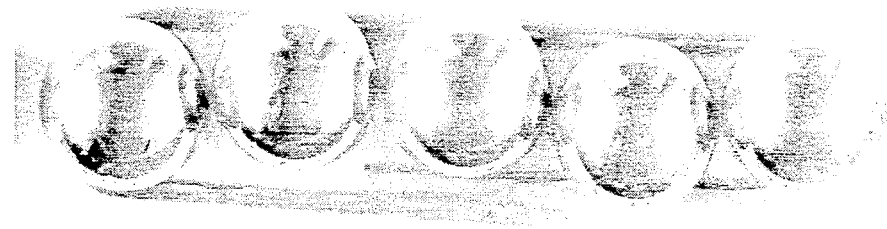
Figure 6:
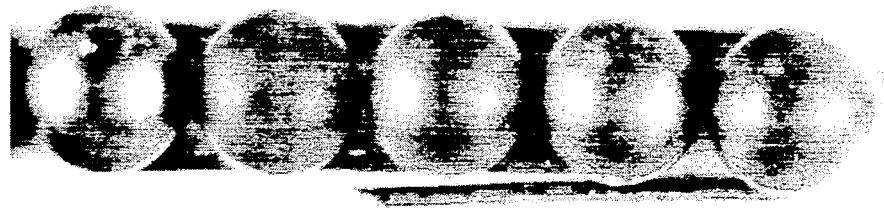

In FIGS. 5 and 6, the carbon steel balls were treated in accordance with the above procedure by bubbling nitric acid vapor into oil containing the balls for 2 hours. FIG. 5 is a photograph of carbon steel balls treated in the 1C1 reference oil having an average IID rust rating of 8.82. FIG. 6 is a photograph of carbon steel balls treated in a 5A2 reference oil having an average IID rust rating of 7.87.

Figure 7:
FIGS. 7 through 11 are photographs of chrome steel balls which have been immersed in various reference oils and treated with corrosive vapor for a period of time.
Figure 8:
Figure 9:

The above procedures were repeated with Chrome steel balls. FIG. 7, 8, and 9 are photographs of chrome steel balls treated in the reference oils having nitric acid vapors bubbled through for 1 hour and 35 minutes. FIG. 7 is the chrome steel balls after treating with the 1C1 reference oil. FIG. 8 is a photograph of chrome steel balls treated in 5A2 reference oil and FIG. 9 is a photograph of chrome steel balls treated with 8C2 reference oil.

Figure 10:
Figure 11:

In FIGS. 10 and 11, the chrome steel balls were treated with the reference oils having nitric acid vapors bubbled through for 2 hours. FIG. 10 is the chrome steel balls after treatment with the 1C1 reference oil and FIG. 11 is the chrome steel balls after treatment with the 5A2 reference oil.

Quantitative methods for determining the amount of corrosion on the balls after treatment may include analyzing the surface of the balls by computer enhanced surface image processing, or by weight loss and/or weight gain techniques. Accordingly, surface image processing techniques provide the most meaningful results compared with other known techniques.

For determining the amount of weight loss after treatment, the corrosion on the balls is removed electrolytically by immersing the balls in a suitable electrolyte for a period of time and applying a direct current to the balls. Suitable electrolytes include aqueous HCl solutions, aqueous HBr solutions, aqueous HF solutions, aqueous $H_2SO_4$ solutions, aqueous $HNO_3$ solutions and the like. Preferably the balls are immersed in a 2 weight percent HCl solution and a voltage of about 14 dc volts is applied to the balls which form the cathode of the electrolytic cell. The anode may be selected from graphite, carbon, titanium, tantalum, platinum or a combination of two or more of the foregoing. Preferably, the anode is platinum.

The period of time for electrolytically treating the balls should be sufficient to remove a substantial amount of the corrosion on the balls. This period of time may range from 1 minute to 1 hour or more. Typically, essentially all of the corrosion is removed in 5 minutes or less.

Subsequent to removing the corrosion, the balls are again cleaned in heptane, dried with nitrogen and weighed. The amount of weight loss is an indication of the amount of corrosion of the balls.

Variations of this invention are within the spirit and scope of the appended claims.

What is claimed is:

1. A bench test method for determining the ability of one or more oleaginous fluid compositions to inhibit corrosion of metal surfaces comprising
    a) providing (i) at least one ball bearing having an arithmetical average surface roughness of less than about 5 microns, (ii) an oleaginous fluid to be tested, and (iii) acid vapor;
    b) immersing said at least one ball bearing in an amount of said oleaginous fluid;
    c) contacting said fluid with said acid vapor at a first temperature and for a first period of time sufficient to dissolve an amount of said acid vapor in the oleaginous fluid, which amount is sufficient to induce oxidation of the surface of said at least one ball bearing;
    d) maintaining said contacted fluid containing said at least one bearing for a second period of time and at a second temperature sufficient to induce oxidation of the at least one bearing surface;
    (e) rating said at least one bearing for corrosion; and
    (f) determining the ability of the oleaginous fluid composition to inhibit corrosion based upon said rating.

2. The method of claim 1 wherein the acid vapor is comprised of at least about 0.5 volume percent nitric acid vapor.

3. The method of claim 1 wherein the first period of time is from about 1.5 to about 4 hours.

4. The method of claim 1 wherein the second period of time is from about 14 to about 18 hours or more.

5. The method of claim 4 wherein the first period of time is from about 1.5 to about 4 hours.

6. The method of claim 5 wherein the acid vapor is comprised of at least about 0.5 volume percent nitric acid vapor.

7. The method of claim 3 wherein the acid vapor is comprised of at least about 0.5 volume percent nitric acid.

8. A method for screening oleaginous fluids comprising
    a) immersing at least one ball bearing having an arithmetical average surface roughness of less than about 5 microns in an oleaginous fluid to be screened;
    b) contacting said oleaginous fluid with acid vapor for a period of time and at a temperature sufficient to form a metal oxide coating on the surface of said at least one ball bearing immersed therein; and
    c) visually determining the amount of metal oxide coating on said at least one ball bearing.

9. The method of claim 8 wherein the acid vapor is comprised of nitric acid vapor.

10. The method of claim 8 wherein the oleaginous fluid is contacted with nitric acid vapor for from about 1.5 to about 4 hours.

11. The method of claim 10 further comprising maintaining the at least one ball bearing immersed in the contacted oleaginous fluid for about 14 to about 18 hours subsequent to said contacting.

12. The method of claim 8 wherein the temperature is in the range of from about 45° to about 55° C.

13. The method of claim 11 wherein the temperature is in the range of from about 45° to about 55° C.

14. The method of claim 8 further comprising analyzing the surface of said at least one ball bearing by computer enhanced surface image processing.

15. The method of claim 13 further comprising analyzing the surface of said at least one ball bearing by computer enhanced surface image processing.

16. The method of claim 15 wherein the acid vapor is comprised of at least about 0.5 volume percent nitric acid vapor.

* * * * *